United States Patent [19]

Sakai

[11] Patent Number: 4,506,079
[45] Date of Patent: Mar. 19, 1985

[54] PROCESS FOR PREPARING INDOLES

[75] Inventor: Makiko Sakai, Kanagawa, Japan

[73] Assignee: Shionogi & Co., Ltd., Osaka, Japan

[21] Appl. No.: 127,521

[22] Filed: Mar. 5, 1980

[30] Foreign Application Priority Data

Mar. 7, 1979 [JP] Japan ............................ 54-27010
Jan. 30, 1980 [JP] Japan ............................ 55-10399

[51] Int. Cl.³ .......................................... C07D 209/04
[52] U.S. Cl. ............................ 548/503; 548/500;
548/501; 548/502; 548/508; 548/491; 548/178;
548/341; 549/341; 549/407; 546/139; 546/165
[58] Field of Search ............... 549/341; 548/503, 500,
548/501, 502, 508

[56] References Cited

U.S. PATENT DOCUMENTS 3,758,502  9/1973  Seemann ........................... 548/503
3,772,329  11/1973  Huyffer ........................... 548/503

Primary Examiner—Robert T. Bond
Attorney, Agent, or Firm—Wenderoth, Lind & Ponack

[57] ABSTRACT

Convenient intermediates for preparing 3-substituted-2-hydroxypropyl aryl ether β-blockers, a reaction to the intermediates of the following formula and a conversion to obtain the said β-blockers are disclosed.

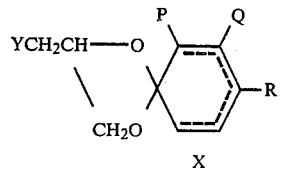

(wherein
X is hydrogen or halogen;
Y is halogen, hydroxy, lower acyloxy, amino, lower alkylamino, lower aralkylamino, lower acylamino, di-lower alkylamino, lower alkyleneamino, N-lower alkyl-N-lower aralkylamino, di-lower acylamino, N-lower alkyl-N-lower acylamino or N-tri-lower alkylsilylamino;
one of P and R combined together with Q represents lower alkylene or alkenylene optionally interrupted by O, N or S and optionally substituted by lower alkyl, lower aralkyl, lower carboxylic acyl, carboxy, protected carboxy; hydroxy, lower alkoxy, lower acyloxy, oxo; amino, lower alkylamino, lower acylamino, nitro, nitroso, lower alkylthio, lower sulfonic acyl or halogen;
and the remaining R or P is hydrogen or halogen;
and dotted line represents the presence of one or two double bonds).

10 Claims, No Drawings

PROCESS FOR PREPARING INDOLES

This invention relates to novel 1,4-dioxaspiro[4,5]-decene compounds of the following formula (I) useful as intermediates for producing 3-substituted-2-hydroxypropyl aryl ethers, the latter compounds being clinical β-blockers:

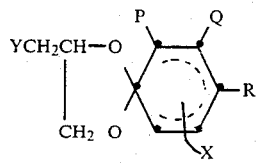

(wherein

X is a hydrogen or halogen;

one of P and R combined together with Q represents lower alkylene or alkenylene optionally interrupted by O, N or S and optionally substituted by lower alkyl, lower aralkyl, lower carboxylic acyl, or carboxy or protected carboxy, hydroxy, lower alkoxy, lower acyloxy, oxo, amino, lower alkylamino, lower acylamino, nitro, nitroso, lower alkylthio, lower sulfonic acyl or halogen; the remaining R or P is hydrogen or halogen;

Y is halogen, hydroxy, lower acyloxy, amino, lower alkylamino, lower aralkylamino, lower acylamino, di-lower alkylamino, lower alkyleneamino, N-lower alkyl-N-lower aralkylamino, di-lower acylamino, N-lower alkyl-N-lower acylamino or N-tri-lower alkylsilylamino; and the dotted line represents the presence of one or two double bonds).

Recently, β-blockers are being evaluated as being useful vasodilators as well as hypotensives. By this invention, a convenient and economic route for producing these β-blockers is provided starting from less expensive starting materials according to the following reaction scheme. Namely, a cyclohexenone compound (II) or its reactive derivative is condensed with a 3-substituted propyleneglycol compound (III) or its reactive derivative in the presence of an acid catalyst (IV) to give a 2-(substituted methyl)-1,4-dioxaspiro[4,5]decene compound (I), which in turn is subjected to aromatization to give an objective 3-substituted-2-hydroxypropyl aryl ether (V):

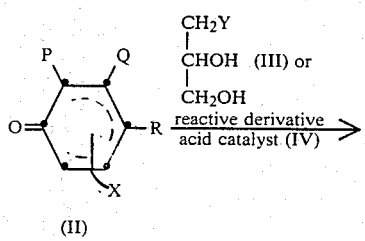

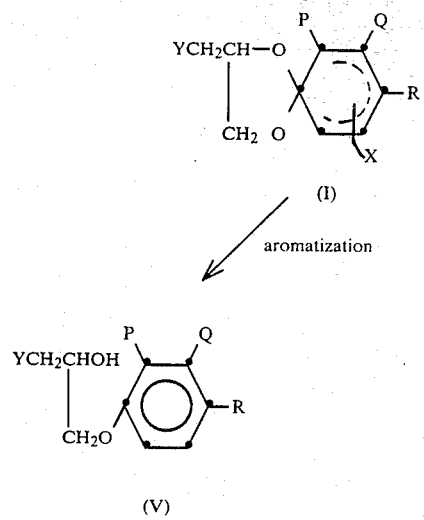

(wherein P, Q, R, X, Y and the dotted line are as defined above)

Throughout this specification, the word lower for the aryl part preferably means $C_6$ to $C_{10}$ and for others means $C_1$ to $C_{10}$; halogen means chlorine, bromine or iodine; and acyl may be an acyl group of a carboxylic, sulfonic, sulfenic, phosphoric or carbonic acid.

[1] COMPOUNDS

The novel 2-(substituted methyl)-1,4-dioxaspiro[4,5]-decene compounds (I) are represented by the following formula:

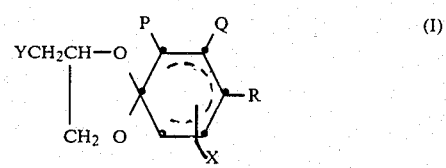

(in which P, Q, R, X, Y and the dotted line are as defined above).

In the above formula, representative lower alkylene as the divalent group bridging Q and P or R includes trimethylene, tetramethylene, pentamethylene, propylene and cyclohexan-1,4-diyl.

Representative lower alkenylene as the divalent group bridging Q and P or R may be 1-propene-1,3-diyl, 1-butene-1,4-diyl, 1-pentene-1,3-diyl or 1,3-butadiene-1,4-diyl.

Representative examples of said alkylene or alkenylene interrupted by a hetero atom selected from O, N and S in its chain include the divalent groups of the following formula:

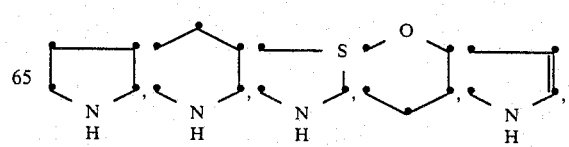

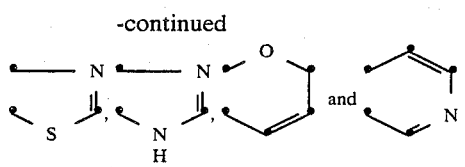

These compounds (I) are useful as intermediates for preparing said β-blockers of formula (V) above by the aromatization as discussed below in this specification.

Some of the representative Compounds (I) are listed below although this is not an exhaustive listing (R=H; $\Delta^6$)

| No. | P—Q combined | X | Y |
|---|---|---|---|
| 1 | —CH=CH—CH=CH— | —H | —Br |
| 2 | —CH=CH—CH=CH— | —Cl | —Br |
| 3 | —CH=CH—CH=CH— | —Br | —Br |
| 4 | —CH=CH—CH=CH— | —Br | —OSO$_2$C$_6$H$_4$CH$_3$—p |
| 5 | —CH=CH—CH=CH— | —Br | —NHCH(CH$_3$)$_2$ |
| 6 | —CH$_2$CH$_2$CONH— | —H | —Br |
| 7 | —CH$_2$CH$_2$CONH— | —Br | —Br |
| 8 | —CH$_2$CH$_2$CONH— | —Br | —NHCH(CH$_3$)$_2$ |
| 9 | —CH=CH—N(COCH$_3$)— | —Br | —NHCH(CH$_3$)$_2$ |
| 10 | —CH=CH—N(COC$_6$H$_5$)— | —H | —Br |
| 11 | —CH=CH—N(COC$_6$H$_5$)— | —Br | —Br |
| 12 | —CH=CH—N(COC$_6$H$_5$)— | —Br | —OSO$_2$C$_6$H$_4$CH$_3$—p |
| 13 | —CH=CH—N(SO$_2$C$_6$H$_5$)— | —H | —Cl |
| 14 | —CH=CH—N(SO$_2$C$_6$H$_5$)— | —Br | —Cl |
| 15 | —CH=CH—N(SO$_2$C$_6$H$_5$CH$_3$—p)— | —H | —Cl |
| 16 | —CH=CH—N(SO$_2$C$_6$H$_4$CH$_3$—p)— | —H | —Br |
| 17 | —CH=CH—N(SO$_2$C$_6$H$_4$CH$_3$—p)— | —H | —NHCH(CH$_3$)$_2$ |
| 18 | —CH=CH—N(SO$_2$C$_6$H$_4$CH$_3$—p)— | —Br | —Cl |
| 19 | —CH=CH—N(SO$_2$C$_6$H$_4$CH$_3$—p)— | —Br | —Br |
| 20 | —CH=CH—N(SO$_2$C$_6$H$_4$CH$_3$—p)— | —Br— | —OH |
| 21 | —CH=CH—N(SO$_2$C$_6$H$_4$CH$_3$—p)— | —Br | —OSO$_2$C$_6$H$_4$CH$_3$—p |
| 22 | —CH=CH—N(SO$_2$C$_6$H$_4$CH$_3$—p)— | —Br | —NHCH(CH$_3$)$_2$ |
| 23 | —CH=CH—N(SO$_2$C$_6$H$_4$CH$_3$—p)— | —Br | —N(CH(CH$_3$)$_2$)(COCH$_3$) |
| 24 | —CH=CH—N(SO$_2$C$_6$H$_4$CH$_3$—p)— | —Br | —N(CH(CH$_3$)$_2$)(COC$_6$H$_5$) |
| 25 | —CH=CH—N(SO$_2$C$_6$H$_4$CH$_3$—p)— | —Br | —N(CH(CH$_3$)$_2$)(SO$_2$C$_6$H$_4$CH$_3$—p) |
| 26 | —CH=CH—N(SO$_2$C$_6$H$_4$CH$_3$—p)— | —Br | —N(CH(CH$_3$)$_2$)(PO(OC$_2$H$_5$)$_2$) |
| 27 | —CH=CH—N(SO$_2$C$_6$H$_4$CH$_3$—p)— | —Br | —N(CH(CH$_3$)$_2$)(P(OC$_2$H$_5$)$_2$) |
| 28 | —CH=CH—N(SO$_2$C$_6$H$_4$CH$_3$—p)— | —Br | —N(CH(CH$_3$)$_2$)(COOCH$_3$) |
| 29 | —CH=CH—N(SO$_2$C$_6$H$_4$CH$_3$—p)— | —Br | —N(CH(CH$_3$)$_2$)(SC$_6$H$_4$NO$_2$—o) |
| 30 | —CH=CH—N(SO$_2$C$_6$H$_4$CH$_3$—p)— | —Br | —N(CH$_2$)$_5$ |
| 31 | —CH=CH—N(SO$_2$C$_6$H$_4$CH$_3$—p)— | —Br | —N(CH(CH$_3$)$_2$)(COCH(CH$_3$)$_3$) |
| 32 | —CH=CH—N(CHO)— | —Br | —N(CH(CH$_3$)$_2$)(COOC$_4$H$_9$—t) |
| 33 | —CH=CH—N(COCH$_3$)— | —Br | —N(CH(CH$_3$)$_2$)(COCH$_3$) |
| 34 | —CH=C(CH$_3$)—N(SO$_2$C$_6$H$_4$CH$_3$—p)— | —Br | —NHCH(CH$_3$)$_2$ |
| 35 | —CH=C(CH$_3$)—N(SO$_2$C$_6$H$_4$CH$_3$—p)— | —Br | —Br |
| 36 | —CH—C(CH$_3$)—N(COCH$_3$)— | —Br | —NHC$_4$H$_9$—t |
| 37 | —N=CH—S— (for Q—R) | —Br | —NHCH(CH$_3$)$_2$ |

| No. | P—Q combined | X | Y |
|---|---|---|---|
| 38 | —CH₂CH₂CO—NH— | —I | —Br |

[2] KETALLIZATION

The novel 2-substituted methyl-1,4-dioxaspiro[4,5]-decene compounds (I) of this invention can be prepared by condensing a cyclohexenone compound (II) or its reactive derivative with a 3-substituted propyleneglycol compound (III) or its reactive derivative in the presence of an acid catalyst (IV) for dehydrating condensation according to the following reaction scheme:

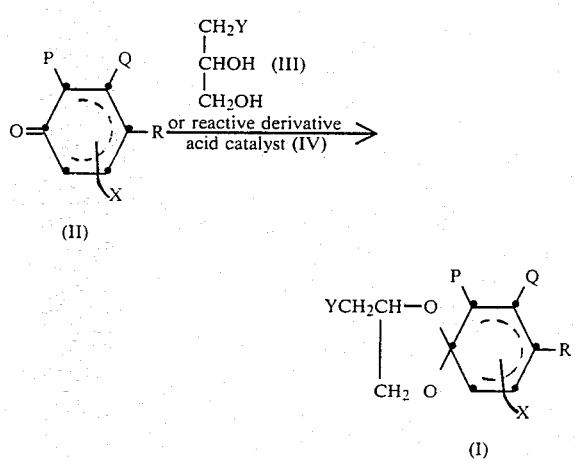

or reactive derivative (wherein P, Q, R, X, Y and the dotted line are as defined above)

Said cyclohexenone compound (II) is a substance known or easily producible by a conventional method from easily available substances. Its reactive derivative can be in ketal, hemiketal, enol ether, acyl hemiacetal, diacyl ketal, enol ester, enamine or like form.

Said 3-substituted propyleneglycol compound (III) is a substance known or easily producible by a known method from easily available substances. Its reactive derivative can be an anhydro derivative (i.e. epoxide), N,N-di-lower alkyl-lower alkanamide acetal, glycol sulfite, O,O-di-lower alkylenedioxysilicone derivative, O,O-lower alkylidene derivative or like reactive form.

Said acid catalyst (IV) can be a mineral acid, lower hydrocarbonsulfonic acid, strong lower carboxylic acid e.g. halogenoacetic acid or Lewis acid. Specific examples of these include hydrochloric acid, sulfuric acid, phosphoric acid, acid ion-exchange resins, oxalic acid, trifluoroacetic acid, methanesulfonic acid, ethanesulfonic acid, benzenesulfonic acid, toluenesulfonic acid, ammonium chloride, calcium chloride, ferric chloride, calcium acetylide, stannic chloride, zinc chloride, boron trichloride, magnesium chloride, aluminum chloride and the like.

This reaction is carried out in an inert solvent. The reaction can be accelerated by removing water formed during the reaction when free glycol (III) is used as the reagent.

Preferable solvents are those which can dissolve the cyclohexenone compound (II) or its reactive derivative and 3-substituted-propyleneglycol compound (III) or its reactive derivative used. More preferable solvents include conventional hydrocarbon-, halogenohydrocarbon-, ether-, ester-, N,N-di-lower alkyl-lower alkana- mide-, nitrile-, sulfoxide-, carboxylic acid-, alcohol- and like solvents and a mixture of two or more of these.

In some cases, compounds (II) or (III) can be used as the solvent. For removing the water formed during the reaction, azeotropic dehydration using e.g. Dean-Stark trap can preferably be applied. Addition of an inert drying material e.g. Molecular Sieves, into the reaction medium is also a preferable choice.

The reaction can be carried out at a temperature range of from minus 50° C. to 150° C. for up to several days.

The reaction of this step is a ketallization well-known to those skilled in the art and well documented e.g. in "Organic Functional Group Preparations", Volume III, pp. 2–53, Academic Press, N.Y. (1972) by Stanley R. Sandler and Wolf Karo.

In a typical example of this ketallization, a solution of a cyclohexenone compound (II) in a halogen-hydrocarbon or aromatic hydrocarbon solvent (5 to 10 parts by weight) is mixed with a 3-substituted propyleneglycol (1 to 5 molar equivalents) and an arylsulfonic acid (0.01 to 0.1 molar equivalent), and the mixed solution is refluxed with heating for 5 to 20 hours under azeotropic dehydration. (Amounts show ratios to cyclohexenone compound (II)). The reaction mixture is made alkaline with aqueous alkali, extracted with a water-immiscible solvent, washed, dried and concentrated to give an objective 1,4-dioxaspiro[4,5]decene compound (I).

In another example of this ketallization, a solution of a cyclohexenone compound (II) and an epihalohydrin (III in a reactive form) (1 to 2 molar equivalents) in a halogenohydrocarbon solvent (5 to 20 parts by weight) is mixed with a solution of stannic chloride (0.1 to 2 molar equivalents) in the same halogenohydrocarbon solvent (0.1 to 1 part by weight), and the mixture is allowed to stand for 3 hours at room temperature. (Amounts show ratios to said cyclohexenone compound (II).) The reaction mixture is made alkaline with aqueous alkali to pH 10 and extracted with a water-immiscible solvent. The extract solution is washed, dried and concentrated to give an objective 1,4-dioxaspiro[4,5]decene compound (I).

1,4-Dioxaspiro[4,5]decene compound (I) thus prepared is usually a diastereomer mixture due to two or three asymmetric carbon atoms at the positions 2 and 4 of 1,3-dioxolane ring part and the position linked to X group when saturated.

[3] HALOGENATION

Action of a halogenating reagent on 1,4-dioxaspiro[4,5]decene compound (I) in which X is hydrogen (Ia) gives the compound (I) where X is halogen (Ib) according to the following scheme:

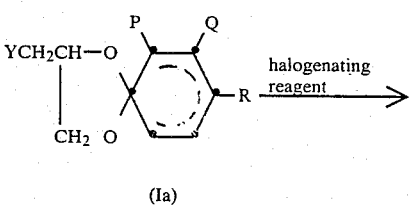

-continued

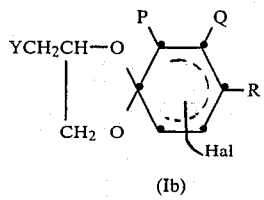

(Ib)

(wherein P, Q, R, Y and dotted line are as defined above and Hal is halogen).

Halogenating reagents used here include molecular halogen, bromine chloride, iodine chloride, quaternary ammonium perhalide, N-haloamide, N-haloimide and other conventional halogenating reagents for this type of reaction. The reaction is, if required, carried out in the presence of acid-acceptor and in a solvent according to a conventional manner to give the halogenated product (Ib).

[4] OTHER MODIFICATION OF 1,4-DIOXASPIRO[4,5]DECENES (I)

(1) Protection and deprotection of reactive groups can be made by a conventional method.

(2) When Y is a leaving group, treatment with a nucleophilic reagent e.g. amine, lower alkylamine, halogenating reagent, water or like, in a conventional manner to give a corresponding compound within the definition.

(3) When Y is amino, lower alkyl, lower aralkyl or lower alkylidene can be introduced to give a 1,4-dioxaspiro[4,5]decene compound (II) having the corresponding substituted amino for Y.

[5] AROMATIZATION

The claimed 1,4-dioxaspiro[4,5]decene compounds (I) where the dotted line represents a double bond and X is halogen, or alternatively, the dotted line shows two double bonds and X is hydrogen can be aromatized to obtain the corresponding 3-substituted-2-hydroxypropyl aryl ether (V) according to the following reaction scheme:

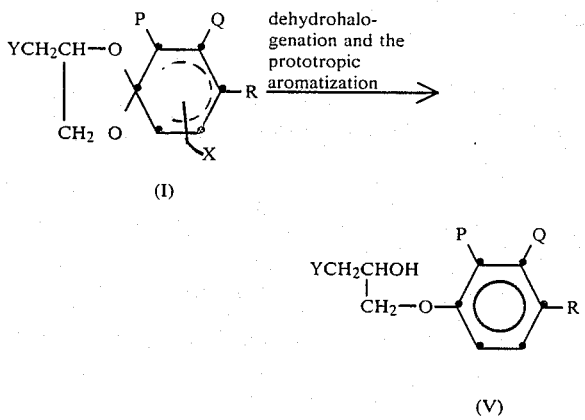

(wherein P, Q, R, X, Y and dotted line are as defined above)

The aromatization is carried out by the action of a base, acid, adsorbing agent, metal salt or heating.

Said starting 1,4-dioxaspiro[4,5]decene compound (I) in which the dotted line represents a double bond and X is halogen can be prepared by the method as given in Sections [2] or [3] of this specification above. Said 1,4-dioxaspiro[4,5]decene compound (I) where the dotted line represents two double bonds and X is hydrogen can be made by a known dehydrohalogenation with a base e.g. aliphatic amine or aromatic amine, if required under heating. An inorganic base and a Lewis acid are also used as reagents for this reaction due to dehydrohalogenation and prototropy.

When said aromatization is carried out with a base, the starting 1,4-dioxaspiro[4,5]decene compound (I) is treated with an aliphatic amine e.g. lower alkylamine, di-lower alkylamine, tri-lower alkylamine, lower alkyleneamine, oxa-lower alkyleneamine, di-lower cycloalkylamine, 1,5-diazabicyclo[5,4,0]undecene-5, 1,4-diazabicyclo[2,2,2]octane, quinuclidine, 1,5-diazabicyclo[4,3,0]nonene-5; aromatic base e.g. pyridine, picoline or quinoline; lower alkanoate, aromatic carboxylate, lower alkoxide, phenolate, carbonate salt of alkali metal; alkali metal hydroxide; or like bases. Generally, this reaction requires higher temperature e.g. 40° to 150° C., for several hours to a few days. Most preferable base is a secondary amine having a boiling point between 80° C. to 200° C.

When said aromatization is carried out with an acid, the starting 1,4-dioxaspiro[4,5]decene compound (I) is treated with a mineral acid, carboxylic acid, sulfonic acid or Lewis acid. However, instability of the starting ketal compound (I) to a proton acid prefers non-protonic acid i.e. Lewis acid for this step of reaction.

When said aromatization is carried out with a Lewis acid, e.g. beryllium chloride, boron trichloride, boron tribromide, magnesium chloride, aluminum chloride, silicon tetrachloride, zirconium tetrachloride, titanium tetrachloride, stannic chloride, antimony trichloride, niobium pentachloride or tellurium tetrachloride; more preferably beryllium chloride, boron trichloride, boron tribromide, aluminium chloride, titanium tetrachloride stannic chloride or other Lewis acid; the reaction proceeds at a very low temperature e.g. −70° to 0° C. The reaction condition depends on the selected Lewis acid. A catalytic amount to excess amount of said Lewis acid per selected starting compound (I) e.g. 1 to 6 molar equivalent may be used. Aromatization of this type is suitable for Compounds (I) having alkylamino or alkenyleneamino as Y. This is done in presence of an additional reagent selected from tertiary amines such as tri-lower alkylamine, N-lower alkyl-lower alkyleneamine, N-lower alkyl-oxa-lower alkyleneamine, N-lower aryl-di-lower alkylamine and polycyclic aza-lower hydrocarbon e.g. 1,4-diazabicyclo[2,2,2]octane, 1-azabicyclo[2,2,2]octane, 1,5-diazabicyclo[5,4,0]undecene-5, 1,5-diazabicyclo[4,3,0]nonene-5 and the like. The amount of the tertiary amine to be added is preferably 1 to 8 molar equivalents per the starting compound (I) for accelerating the reaction and improve the yield.

This reaction is carried out at sub-zero to room temperature, preferably at −80° C. to 20° C. The reaction is usually complete within 0.1 to 50 hours. The reaction time varies considerably depending on choosed reaction conditions e.g. solvent, selected sort of Lewis acid and/or the presence or absence and sort of the additional reagent.

In a typical example of this aromatization, a mixture of 1,4-dioxaspiro[4,5]decene compound (I), an oxa-lower alkyleneamine compound (5 to 10 or up to 30 parts by weight when utilized also as the solvent) and optionally an aromatic hydrocarbon solvent (5 to 10 parts by weight) is heated at reflux for 5 to 10 hours, and diluted with with water and ethyl acetate. The formed organic layer is taken up and washed, dried and evaporated to give the objective 3-substituted-2-hydroxypropyl aryl ether (V).

In another typical example of this aromatization, a solution of 1,4-dioxaspiro[4,5]decene compound (I) and a tri-lower alkylamine (1 to 8 molar equivalents) in a halogenohydrocarbon solvent (10 to 20 parts by weight) cooled at $-50°$ to $-10°$ C. is mixed dropwise with a solution of a stannic halide (1 to 5 molar equivalents) in the same or different halogenohydrocarbon solvent (1 to 10 parts by weight), kept at the same temperature for a few minutes, warmed to room temperature and allowed to stand at the same temperature for 1 to 10 hours. (Amounts show ratios to the 1,4-dioxaspiro[4,5]decene compound (I)). The reaction mixture is evaporated, made alkaline with aqueous alkali, shaken and extracted with a water-immiscible solvent and extract solution worked up as usual to give an objective 3-substituted-2-hydroxypropyl aryl ether (V).

Said aromatization with an adsorbing agent can be carried out with e.g. alumina, silica gel, magnesium silicate, calcium carbonate, zinc oxide, etc.

Said aromatization by heating can be carried out and at an elevated temperature sufficient to cause pyrolytic dehydrohalogenation e.g. at around 150° C. preferably in an inert solvent.

The above aromatizations are carried out in an inert solvent e.g. hydrocarbon-(e.g. benzene, toluene, xylene, ligroin), halogenohydrocarbon-(e.g. chlorobenzene, dichloromethane, dichloroethane, trichloroethane, chloroform), ether-(e.g. diethyl ether, dibutyl ether, dioxane), nitrohydrocarbon-(e.g. nitrobenzene, nitromethane), ester-(e.g. ethyl benzoate, ethyl acetate), amine-, amide-, nitrile- or alcohol-solvent or mixture of two or more of these. When selected reagent is a liquid, it may also serve as a solvent.

When said dehydrohalogenation in Part [5] is carried out by the action of a base or Lewis acid, this aromatization often follows immediately to allow the two reactions proceed in one handling to afford the objective 3-substituted-2-hydroxypropyl aryl ether (V) directly from 1,4-dioxaspiro[4,5]decene compound (I). However, as the reaction course of this simultaneous dehydrohalogenation and aromatization has not been elucidated, intermediacy of the diene compound (I) is still open to arguementation especially in the case of Lewis acid catalyzing the reaction.

Above said aromatization products can be isolated by removing unreacted starting materials, excess reagent, solvent, by-product, etc. from the reaction mixture by a conventional manner (e.g. concentration, washing, adsorption, extraction, precipitation, crystallization) and purifying by a conventional method (e.g. fractional extraction, recrystallization, washing, adsorption, elution, chromatography).

If required, the reaction products or crude material can be used as the starting materials for succeeding reactions without isolation or further purification.

The product, 3-substituted-2-hydroxypropyl aryl ther (V), is a $\beta$-blocker for treating circulatory diseases, as explained above. The compound (V) can be, if required, deprotected, protected or modified at the P, Q, R or Y group to obtain more pharmacologically preferable substances and serve as intermediates therefor.

[6] EXAMPLES

Following examples are given to further illustrate the embodiment of this invention, but not intended to restrict the scope thereof. In the examples, structural formulas are plain formulas neglecting stereochemical structure. All "parts" showing the amount of material are parts by weight.

EXAMPLE I (KETALLIZATION)

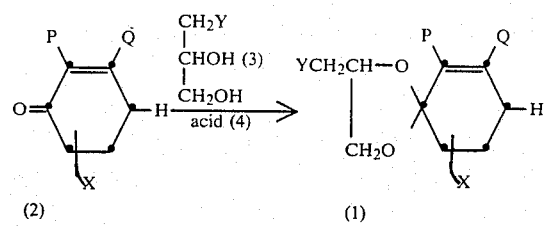

A mixture of the cyclohexenone compound (2) (100 parts), p-toluenesulfonic acid (0.1 molar equivalent), 3-substituted-propyleneglycol compound (3) (1 to 5 molar equivalents) and toluene (500 to 5000 parts) is refluxed for about 2 to 48 hours under azeotropic dehydration. After cooling, the reaction mixture is neutralized with diluted aqueous sodium hydroxide and toluene layer is separated. The organic layer is washed with water, dried and concentrated to dryness under reduced pressure. The obtained residue is purified to give the objective 2-(Y-substituted methyl)-1,4-dioxaspiro[4,5]-decene compound (I) having the physical constants given in the following Table I, Parts 1 to 7.

When Y is a basic group, it should be neutrallized beforehand with a suitable acid e.g. p-toluenesulfonic acid.

TABLE I

Physical constants of

YCH₂CH—O, CH₂ O (structure shown with P, Q, X, H substituents) (I)

| No. | P—Q | X | Y | IR: $\nu_{max}^{film}$ cm$^{-1}$ | NMR: $\delta_{ppm}^{CDCl_3}$ (Hz values show coupling constant) |
|---|---|---|---|---|---|
| 1 | 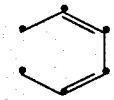 | —H | —Br | 1606, 1059. | 1.67–2.25m4H, 3.55–3.05m2H, 3.17–4.87m5H, 6.81–7.81m4H. |

TABLE I-continued

Physical constants of (I)

$$YCH_2CH-O\underset{CH_2\ O}{\overset{P\quad Q}{\diagdown}}\underset{X}{\diagup}H$$

| No. | P—Q | X | Y | IR: $\nu_{max}^{film}$ cm$^{-1}$ | NMR: $\delta_{ppm}^{CDCl_3}$ (Hz values show coupling constant) |
|---|---|---|---|---|---|
| 2 | (cyclohexene) | —Br | —Br | 1613, 1077. (CHCl$_3$) | 2.23–2.77m2H, 2.77–3.30m2H, 3.30–3.83m2H, 3.83–5.03m4H, 6.93–7.77m4H. |
| 3 | (cyclohexene) | —Br | —O—SO$_2$—C$_6$H$_4$—CH$_3$ | 1605, 1374, 1180, 987. (CHCl$_3$) | [2.42s + 2.21–3.12m]7H, 3.89–4.28m6H, 6.99–7.55m6H, 7.67–7.92m2H. |
| 4 | (cyclohexene) | —Br | —NHCH(CH$_3$)$_2$ | 3340, 1609, 1072. | [1.05d(6.5Hz) + 1.08d(6.5Hz)]6H, 1.51s1H, 2.09–3.38m7H, 3.79–4.84m4H, 6.99–7.70m4H. |
| 5 | (lactam ring) | —Br | —Br | 3090, 1653, 1378, 1296, 1050.(KBr) | 1.63–2.69m10H, 3.17–4.57m5H, 6.22brs1H. |
| 6 | (N-CO-phenyl ring) | —H | —Br | — | 1.65–2.35m4H, 2.77–3.20m2H, 3.20–4.80m5H, [6.05d(3Hz) + 6.10d(3Hz)]1H, 6.69d(3Hz)1H, 7.3–7.8m5H. (CCl$_4$) |
| 7 | (N-CO-phenyl ring) | —Br | —Br | 1702, 1317. (CHCl$_3$) | 2.23–2.76m2H, 2.84–3.43m2H, 3.43–3.67m2H, 3.86–4.85m3H, [6.22d(3.5Hz) + 6.33d(3.5Hz)]1H, 7.34–7.88m5H. |
| 8 | (N-CO-phenyl ring) | —Br | —OSO$_2$—C$_6$H$_4$—CH$_3$ | 1700, 1360, 1316, 1268, 1196, 1179. | — |
| 9 | (N-SO$_2$-phenyl ring) | —H | —Cl | 1596, 1372, 1172, 1116. | — |
| 10 | (N-SO$_2$-phenyl ring) | —Br | —Cl | 1601, 1373, 1182, 1111. | 2.21–2.51m2H, 2.41brt(6Hz)2H, 2.85brt(6Hz)2H, 2.65–3.01 m2H, 3.48–3.81m2H, 3.81–4.83 m4H, 6.12–6.41m1H, 7.08–7.88m 6H. (CDCl$_3$) |

TABLE I-continued

Physical constants of [structure (I): YCH$_2$CH-O / CH$_2$-O cyclohexene ring with P, Q, H, X substituents]

| No. | P—Q | X | Y | IR: $\nu_{max}^{film}$ cm$^{-1}$ | NMR: $\delta_{ppm}^{CDCl_3}$ (Hz values show coupling constant) |
|---|---|---|---|---|---|
| 11 | N-SO$_2$-(C$_6$H$_4$)-CH$_3$ (vinyl-N) | —H | —Cl | 1600, 1371, 1172, 1152. | 1.58–2.20m4H, 2.41s3H, 2.52–2.85m2H, 3.33–3.69m2H, 3.69–4.57m3H, [6.13d(3Hz) + 6.18d(3Hz)]1H, 7.12–7.17m3H, 7.62d(8.5Hz)2H.(CDCl$_3$ + CCl$_4$) |
| 12 | N-SO$_2$-(C$_6$H$_4$)-CH$_3$ | —H | —Br | 1600, 1372, 1173, 1115. | 1.50–2.09m4H, 2.36s3H, 2.49–2.80m2H, 3.15–3.54m2H, 3.54–4.61m3H, [6.10d(3Hz) + 6.15d(3Hz)]1H, [7.59d(8.5Hz) + 7.20d(8.5Hz)]A$_2$B$_2$4H. (CCl$_4$) |
| 13 | N-SO$_2$-(C$_6$H$_4$)-CH$_3$ | —H | —NH—i-C$_3$H$_7$ | 3350, 1600, 1372, 1173, 1112. | 1.01d(6.5Hz)6H, 1.60–1.99m4H, 2.40s3H, 2.50–2.93m5H, 3.53–4.43m3H, [6.09d(3Hz) + 6.12d(3Hz)]1H, 7.08d(3Hz)1H, [7.24d(8.5Hz) + 7.62d(8.5Hz)]A$_2$B$_2$4H, (CCl$_4$) |
| 14 | N-SO$_2$-(C$_6$H$_4$)-CH$_3$ | —Br | —Cl | 1597, 1370, 1174, 1120.(KBr) | [2.42s + 2.14–2.68m]5H, 2.68–3.11m2H, 3.51–3.93m2H, 3.93–4.88m4H, 6.11–6.44m1H, 7.13–7.44m3H, 7.67d(8Hz)A$_2$B$_2$2H.(CDCl$_3$) |
| 15 | N-SO$_2$-(C$_6$H$_4$)-CH$_3$ | —Br | —Br | 1604, 1381, 1178, 1119. (CHCl$_3$) | — |
| 16 (diastereomer mixture 1) | N-SO$_2$-(C$_6$H$_4$)-CH$_3$ | —Br | —OH | 3450, 1597, 1371, 1176, 1120.(KBr) | [2.42s + 1.99–2.63m + 2.63–3.20m]8H, 3.39–4.75m6H, 6.31d(3.5Hz)1H, [7.25d(3.5Hz) + 7.30d(8Hz)A$_2$B$_2$)]3H, 7.69d(8Hz)A$_2$B$_2$2H. |
| 17 (diastereomer mixture 2) | N-SO$_2$-(C$_6$H$_4$)-CH$_3$ | —Br | —OH | 3440, 1598, 1372, 1175, 1122.(KBr) | [2.43s + 2.24–2.72m + 2.72–3.10m]7H, 3.40–4.77m6H, 6.27–6.47m1H, 7.20–7.51m3H, 7.73d(8Hz)A$_2$B$_2$2H. |

TABLE I-continued

Physical constants of (I):

$$YCH_2CH(CH_2O-)(O-) \text{ cyclohexene ring with P, Q, H, H, X substituents}$$

| No. | P—Q | X | Y | IR: $\nu_{max}^{film}$ cm$^{-1}$ | NMR: $\delta_{ppm}^{CDCl_3}$ (Hz values show coupling constant) |
|---|---|---|---|---|---|
| 18 | (CH=N–SO$_2$–C$_6$H$_4$–CH$_3$) | —Br | —O—SO$_2$—C$_6$H$_4$—CH$_3$ | 1600, 1370, 1179, 1123. (KBr) | [2.42s + 2.45s + 2.22–2.58m]8H, 2.65–3.05m2H, 3.90–4.78m6H, [6.18d(3.5Hz) + 6.21d(3.5Hz)]1H, 7.10–7.91m9H.(CDCl$_3$) |
| 19 | (CH=N–SO$_2$–C$_6$H$_4$–CH$_3$) | —Br | —NHCH(CH$_3$)$_2$ | 3350, 1604, 1380, 1184, 1126. | 1.04d(6.5Hz)6H, 1.45s1H, 2.40s3H, 2.10–3.07m7H, 3.67–4.67m4H, 6.25d(3Hz)1H, 7.63d(8Hz)2H, 7.07–7.40m3H. (CDCl$_3$) |
| 20 | (CH=N–SO$_2$–C$_6$H$_4$–CH$_3$) | —Br | —N(COCH$_3$)(CH(CH$_3$)$_2$) | 1630–1640, 1598, 1370, 1171, 1121. (CHCl$_3$) | 1.10–1.38m6H, [2.13s + 2.41s + 2.20–2.65m + 2.65–3.00m]10H, 3.00–4.67m7H, [6.25d(3.5Hz) + 6.35d(3.5Hz)]1H, 7.12–7.44 m3H, 7.69d(8.5Hz)A$_2$B$_2$2H. |
| 21 | (CH=N–SO$_2$–C$_6$H$_4$–CH$_3$) | —Br | —N(CO–C$_6$H$_5$)(CH(CH$_3$)$_2$) | 1624, 1376, 1174, 1121. (KBr) | — |
| 22 | (CH=N–SO$_2$–C$_6$H$_4$–CH$_3$) | —Br | —N(SO$_2$–C$_6$H$_4$–CH$_3$)(CH(CH$_3$)$_2$) | 1600, 1374, 1334, 1190, 1172, 1152, 1121. (KBr) | — |
| 23 | (CH=N–SO$_2$–C$_6$H$_4$–CH$_3$) | —Br | —N(PO(OC$_2$H$_5$)$_2$)(CH(CH$_3$)$_2$) | 1599, 1371, 1248, 1175, 1123, 1021, 963. | — |
| 24 | (CH=N–SO$_2$–C$_6$H$_4$–CH$_3$) | —Br | —N(P(OC$_2$H$_5$)$_2$)(CH(CH$_3$)$_2$) | 1600, 1372, 1177, 1122, 1038. | — |
| 25 | (CH=N–SO$_2$–C$_6$H$_4$–CH$_3$) | —Br | —N(COOCH$_3$)(CH(CH$_3$)$_2$) | 1693, 1601, 1462, 1374, 1176, 1126. | 0.97–1.29m6H, 2.43s3H, 2.20–2.66m5H, 2.66–2.97m2H, 3.68s3H, 2.97–4.62m7H, [6.22d(3.5Hz) + 6.29 d(3.5Hz)]1H, 7.10–7.40m3H, 7.66 (8.5Hz)A$_2$B$_2$2H |

TABLE I-continued

Physical constants of (I)

$$YCH_2CH-O \begin{array}{c} P \quad Q \\ \diagup \\ \diagdown \\ CH_2 \quad O \end{array} H$$

| No. | P—Q | X | Y | IR: $\nu_{max}^{film}$ cm$^{-1}$ | NMR: $\delta_{ppm}^{CDCl_3}$ (Hz values show coupling constant) |
|---|---|---|---|---|---|
| 26 | (N-SO₂-C₆H₄-CH₃ vinyl) | —Br | O₂N-C₆H₄-S-N(CH(CH₃)₂) | 1591, 1565, 1512, 1368, 1333, 1303, 1178, 1120 (KBr) | — |
| 27 | (N-SO₂-C₆H₄-CH₃ vinyl) | —Br | —N(piperidine) | 1600, 1374, 1174, 1126. (KBr) | — |

EXAMPLE I-1

Detailed preparation of the compound No. 10 in preceding Table I is given to illustrate the ketallization.

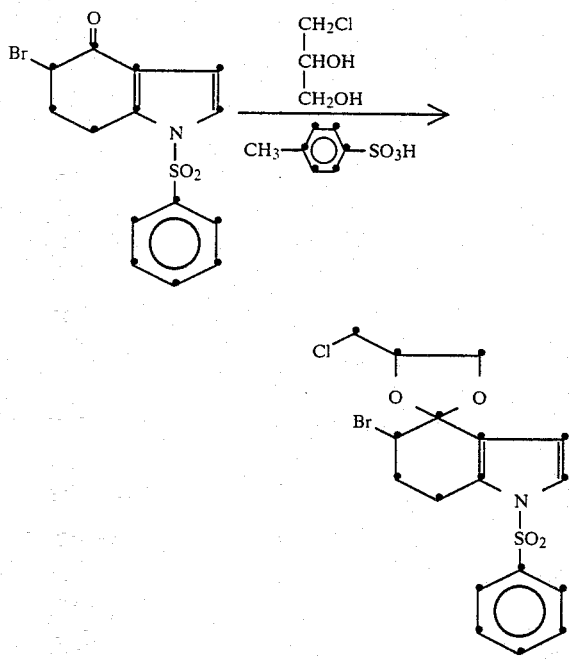

In a three necked flask equipped with a thermometer, a stirrer and a reflux condenser having Widmer-type water trap filled with Molecular Sieves are placed 4-oxo-5-bromo-1-benzenesulfonyl-4,5,6,7-tetrahydroindole (100 parts), 3-chloro-1,2-propanediol (311 parts), p-toluenesulfonic acid monohydrate (3 parts) and toluene (4500 parts), and the mixture is refluxed for 7 hours 20 minutes while drying the refluxing azeotropic mixture. After cooling, the reaction mixture is adjusted to pH 9 with 2.5N aqueous sodium hydroxide with stirring, and the formed toluene layer is separated. The water layer is washed with benzene (200 parts). Toluene layer and benzene washing are combined, washed twice with water (500 parts) and dried over anhydrous sodium sulfate (500 parts). The drying agent is filtered off, and the filtrate is concentrated under reduced pressure. The obtained residue (143 parts) is dissolved in benzene (300 parts), stirred with active charcoal (50 parts) for 30 minutes and filtered through a filter-bed of siliceous earth. The filtrate is concentrated under reduced pressure, and stirring of resulted residue with a small amount of ether and hexane affords amorphous powder. This is collected by filtration, washed with a mixture of ether and hexane, and dried to give 4'-chloromethyl-5-bromo-1-benzenesulfonyl-4,5,6,7-tetrahydroindole-4-spiro-2'-[1,3]-dioxolane diastereomer mixture (122 parts) in 97% yield.

EXAMPLE I-2

An example of reactive derivative of 3-substituted propylene glycol compound (3) in O,O-isopropylidene form.

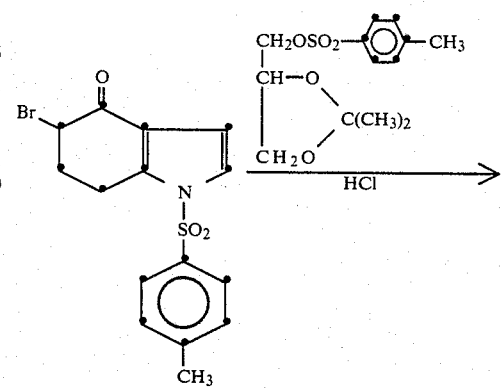

-continued

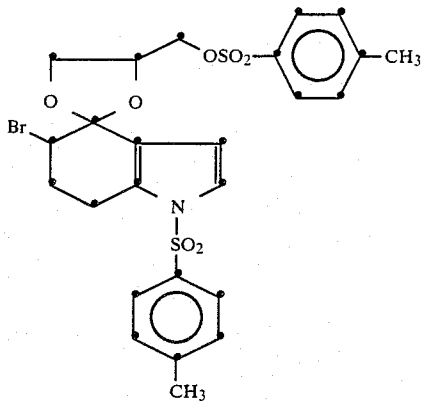

A mixture of 3-p-toluenesulfonyloxypropyleneglycol acetonide (2 molar equivalents), 5-bromo-1-p-toluenesulfonyl-4-oxo-4,5,6,7-tetrahydroindole (100 parts), hydrochloric acid (1 molar equivalent) and benzene (500 to 2000 parts) is refluxed for 21 hours under azeotropic dehydration. After cooling, the reaction mixture is adjusted to pH 10 with 5N-sodium hydroxide, shaken and water layer drained. Organic layer is washed with water, (100 parts) and dried over anhydrous sodium sulfate (50 parts). The drying agent is removed by filtration. The filtrate is then concentrated under reduced pressure at a temperature below 50° C. to leave amorphous 4'-p-toluenesulfonyloxy-1-p-toluenesulfonyl-5-bromo-4,5,6,7-tetrahydroindole-4-spiro-2'-[1,3]-dioxolane diastereomer mixture in 42% yield. The product is shown in Table I, Part 6, No. 18.

EXAMPLE I-3

An example of reactive derivative of 3-substituted propyleneglycol compound (3) in anhydro form.

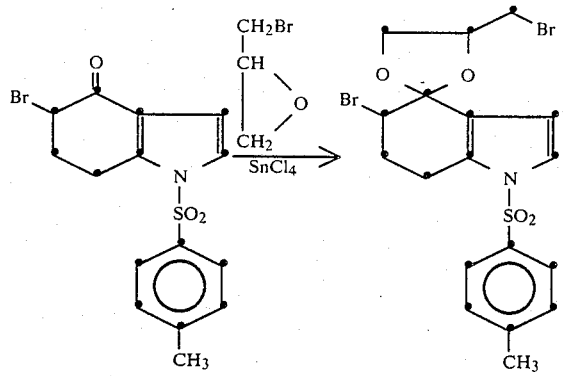

A mixture of 5-bromo-1-p-toluenesulfonyl-4-oxo-4,5,6,7-tetrahydroindole (100 parts), epibromohydrin (1.2 molar equivalents) and stannic chloride (0.1 molar equivalent) in carbon tetrachloride (1500 parts) is kept at 0° C. to 2° C. for 19 hours. The reaction mixture is carefully mixed with 5N-sodium hydroxide to adjust at pH 10, shaken and organic layer separated. By washing with water, drying and concentration, the organic layer gives 72.3% yield of 5-bromo-4'-bromomethyl-1-p-toluenesulfonyl-4,5,6,7-tetrahydroindole-4-spiro-2'-[1,3]dioxolane diastereomer mixture. Amounts show ratios to the starting 5-bromo-1-p-toluenesulfonyl-4,5,6,7-tetrahydroindole-4-one.

The physical constants of the product is shown in Table I, No. 15.

EXAMPLE II (HALOGENATION)

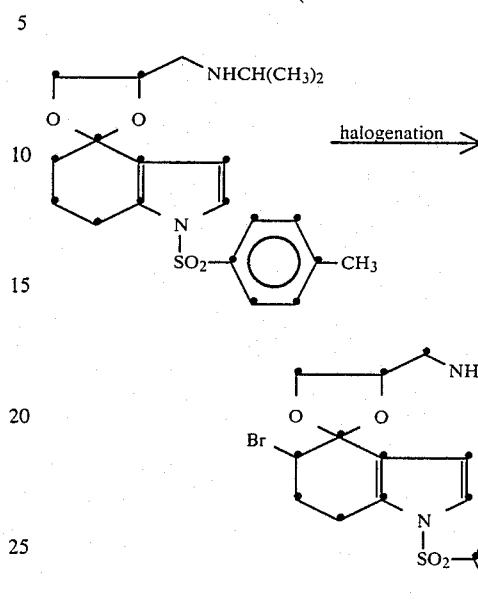

(1) with cupric bromide.

To a solution of 4'-isopropylaminomethyl-1-p-toluenesulfonyl-4,5,6,7-tetrahydroindole-4-spiro-2'-[1,3]-dioxolane (100 parts) in t-butanol (2000 parts) is added cupric bromide (2.5 molar equivalents) and the mixture is heated under reflux for 4 hours. After cooling, the mixture is filtered to remove solid material and adjusted at pH 10 with 5N-sodium hydroxide aqueous solution. The mixture is extracted with ethylene chloride. The organic layer is separated, washed with water, dried and concentrated to afford 5-bromo-4'-isopropylaminomethyl-1-p-toluenesulfonyl-4,5,6,7-tetrahydroindole-4-spiro-2'-[1,3]dioxolane in 70% yield.

(2) with pyridine hydrobromide bromine complex.

To a solution of 4'-isopropylaminomethyl-1-p-toluenesulfonyl-4,5,6,7-tetrahydroindole-4-spiro-2'-[1,3]-dioxolane (100 parts) in dioxane (1000 parts) is added pyridine hydrobromide-bromine complex (2 molar equivalents) and heated at 40° to 50° C. for 1 hour. After cooling, the mixture is diluted with 5N-sodium hydroxide aqueous solution and extracted with dichloromethane. The extract solution is washed with water, dried and concentrated to afford 5-bromo-4'-isopropylaminomethyl-1-p-toluenesulfonyl-4,5,6,7-tetrahydroindole-4-spiro-2'-[1,3]dioxolane in 65% yield. The products are shown in Table I, No. 19.

EXAMPLE III (MODIFICATION OF THE STRUCTURE)

(1) Acylation.

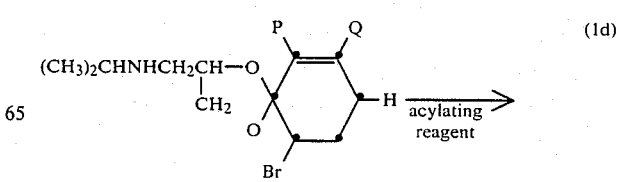

-continued

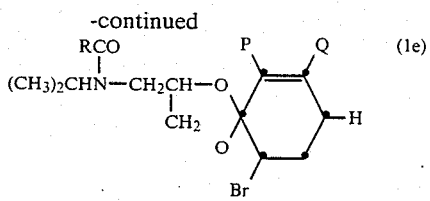

To an ice-cooled mixture of a compound (1d) (100 parts) and a base (and a solvent) is added an acylating reagent (1 to 9 equivalents), and the mixture is let stand until the starting compound disappears. The reaction mixture is concentrated under reduced pressure and washed to remove the base. The remaining residue is dissolved in dichloromethane and water, and formed organic layer is separated. The organic layer is washed with water, dried and concentrated under reduced pressure. The residue is purified to give the corresponding acylate(1e).

Table II illustrates some reaction conditions.

-continued

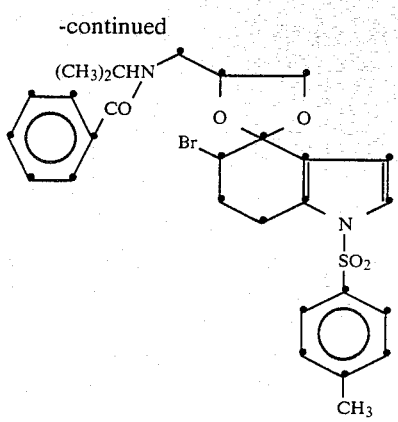

A solution of 4'-isopropylaminomethyl-1-p-toluenesulfonyl-5-bromo-4,5,6,7-tetrahydroindole-4-spiro-2'-[1,3]dioxolane (100 parts) dissolved in pyridine (343 parts) is prepared and placed in a three necked

TABLE II

| No. | Compound (Id) P—Q | Part | Acylation Acylating reagent R | Activation (Part) | Basic Solvent (Part) | Temp. (°C.) | Time (hr) | Compound (1e) Crop (Part) | Yield (%) |
|---|---|---|---|---|---|---|---|---|---|
| 1 | (pyrrole-N-SO2-C6H4-CH3) | 100 | $CH_3CO-$ | Anhydride 32 | $C_5H_5N$ 440 | rt | 12 | 99 | 91 |
| 2 | " | 100 | $C_6H_5CO-$ | chloride 35 | $C_5H_5N$ 343 | rt | 14 | 111 | 91 |
| 3 | " | 100 | (2-$NO_2$-$C_6H_4$-S—) | chloride 39 | $(CH_3)_3N$ 89 $CH_2Cl_2$ 2690 | rt | 96 | 131 | 99 |
| 4 | " | 100 | $t-C_4H_9CO$ | chloride 9 | $C_5H_5N$ 14 | rt | 39 | 79 | 67 |

Detailed reaction procedure of Table II, No. 2 is given below as a representative example.

(No. 2)

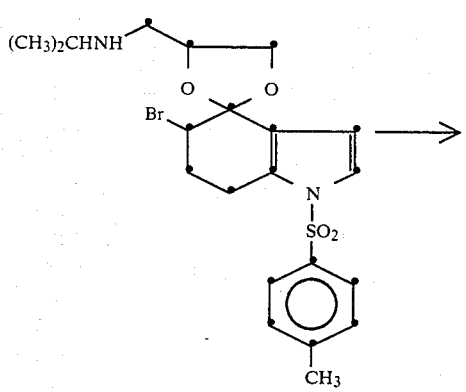

flask equipped with a stirrer and a thermometer. Benzoyl chloride (35 parts) is added dropwise at 0° C. to 5° C. After standing at room temperature for 14 hours, the reaction mixture is evaporated to remove pyridine at below 70° C. Obtained residue is dissolved in dichloromethane (300 parts) and washed three times with water (50 parts). Aqueous washings are combined and washed with dichloromethane (50 parts). Dichloromethane solution and dichloromethane washing are combined, washed with water (30 parts), are dried over anhydrous sodium sulfate. After 1 hour, the drying agent is removed by filtration, and obtained filtrate is concentrated to dryness under reduced pressure. Obtained residue (132 parts) is dissolved in dichloromethane (270 parts), allowed to stand for half an hour with active charcoal (30 parts), and filtered through Florisil filter-bed. The resulting filtrate is concentrated under reduced pressure to dryness at below 30° C. and the obtained residue is triturated in a small amount of a mixture of benzene and dichloromethane to give amorphous powder. The product is collected by filtration and dried to give 4'-(N-isopropyl-N-benzoylaminomethyl)-1-p-toluenesulfonyl-5-bromo-4,5,6,7-tetrahydroindole-4-spiro-2'-[1,3]dioxolane (111 parts) in 91.5% yield.

(2) Nucleophilic substitution at Y.

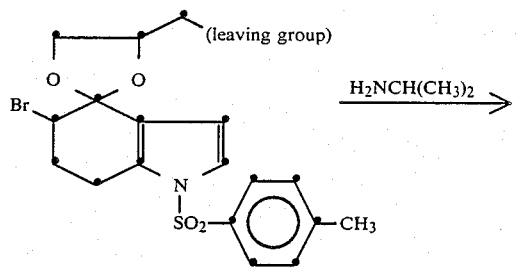

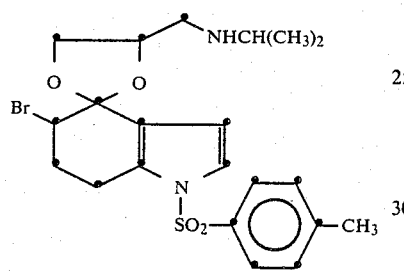

A solution of 4'-chloromethyl-5-bromo-1-p-toluenesulfonyl-4,5,6,7-tetrahydroindole-4-spiro-[1,3]dioxolane (100 parts) in isopropylamine (890 parts) is placed in a sealed tube and heated on boiling water bath for 7 hours. The reaction mixture is evaporated to remove isopropylamine. The residue is dissolved in dichloromethane, washed with water, dried and concentrated to afford 4'-isopropylaminomethyl-5-bromo-1-p-toluenesulfonyl-4,5,6,7-tetrahydroindole-4-spiro-[1,3]dioxolane in 60% yield. The physical constants are given in Table I, No. 19. yield. The physical constants are given in Table I, No. 19.

The same product can be prepared in 70 to 80% yield by heating 4'-bromomethyl-5-bromo-1-p-toluenesulfonyl-4,5,6,7-tetrahydroindole-4-spiro-[1,3]dioxolane or 4'-p-toluenesulfonyloxymethyl-5-bromo-1-p-toluenesulfonyl-4,5,6,7-tetrahydroindole-4-spiro-2'-[1,3]dioxolane in isopropylamine for 18 hours.

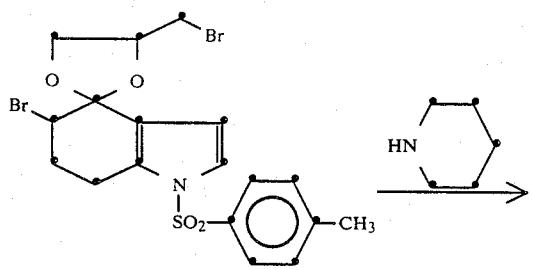

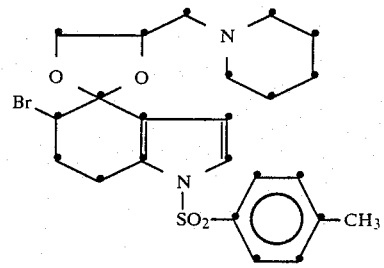

Heating of 4'-bromomethyl-5-bromo-1-p-toluenesulfonyl-4,5,6,7-tetrahydroindole-4-spiro-2'-[1,3]dioxolane with piperidine at 80° C. for 3 hours affords 4'-piperidinomethyl-5-bromo-1-p-toluenesulfonyl-4,5,6,7-tetrahydroindole-4-spiro-2'-[1,3]dioxolane in 75% yield.

(3) O-Acylation.

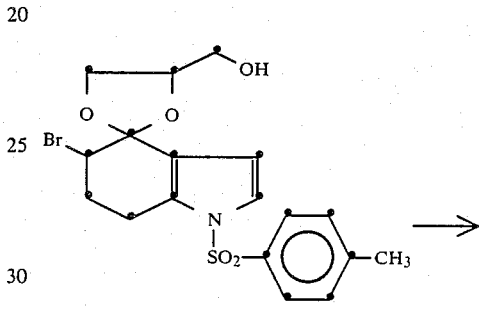

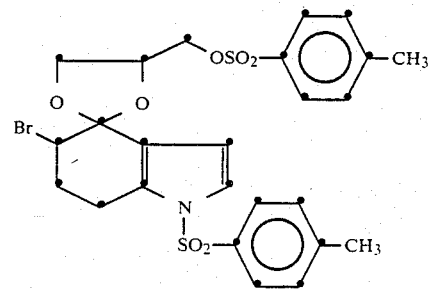

To a solution of 4'-hydroxymethyl-5-bromo-1-p-toluenesulfonyl-4,5,6,7-tetrahydroindole-4-spiro-[1,3]-dioxolane (100 parts) in dichloromethane (2000 parts) is added a solution of p-toluenesulfonyl chloride (1.1 molar equivalent) and pyridine (1.2 molar equivalents) in dichloromethane (500 parts), and the mixture is kept at room temperature for 10 hours. The mixture is evaporated, and the residue is dissolved in ethyl acetate, washed with water, dried and evaporated to give 4'-p-toluenesulfonyloxymethyl-5-bromo-1-p-toluenesulfonyl-4,5,6,7-tetrahydroindole-4-spiro-[1,3]dioxolane in 87% yield. The physical constants are given in Table I, No. 18.

EXAMPLE IV (AROMATIZATION WITH AN ORGANIC BASE)

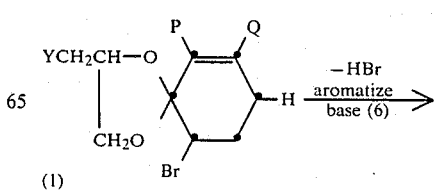

(1)

-continued

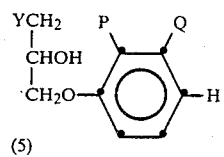
(5)

A mixture of a 2-substituted-1,4-dioxaspiro[4,5]decene (1) (100 parts), a base (6) (1 to 5 molar equivalents) and a solvent (500 to 2000 parts) are heated at 75° to 120° C. for 3 to 50 hours. After cooling, the reaction mixture is diluted with water and ethyl acetate. Formed organic layer is separated and washed with water, dried and concentrated to dryness. The residue is purified to give a 3-substituted-2-hydroxypropyl aryl ether (5).

Reaction conditions are given in Table III and physical constants of some products are given in Table IV.

TABLE III

| | Aromatization with a base | | | | | | | |
|---|---|---|---|---|---|---|---|---|
| | Compound (1) | | | Base* | Solvent | Temp. | Time | Product (5) |
| No. | P—Q | Y | Part | (Part) | (Part) | (°C.) | (hr) | Crop (Part) Yield (%) |
| 1 | ![vinyl-N-SO2-tolyl] | —NH—i-$C_3H_7$ | 100 | DBN 54 | — | 85 | 6.5 | 33    40 |
| | | | 100 | DBU 169 | $C_6H_5CH_3$ 553 | 75 | 17 | 29    35 |
| 2 | " | —Cl | 700 | DBU 68 | i-$C_3H_7NH_2$ 817 | reflux | 17 | 31    35 Cl as Y group changed to —NH—i-$C_3H_7$ during reaction. |
| 3 | " | —Br | 100 | DBU 73 | i-$C_3H_7NH_2$ 666 | reflux | 16 | 37    46 Br as Y group changed to —NH—i-$C_3H_7$ during reaction. |
| 4 | " | —N(i-$C_3H_7$)(COCH$_3$) | 100 | DBU 145 | $C_6H_5CH_3$ 673 | 90 | 48 | 34    40 |
| 5 | " | —N(i-$C_3H_7$)(CO-phenyl) | 100 | DBU 51 | $HCON(CH_3)_2$ 319 | 85 | 24 | 35    41 |
| 6 | " | —N(i-$C_3H_7$)(COC(CH$_3$)$_3$) | 100 | DBU 54 | $HCON(CH_3)_2$ 115 | 100 | 15.5 | 39    46 |
| 7 | " | —N(i-$C_3H_7$)(S-(o-nitrophenyl)) | 100 | DBU 158 | $HCON(CH_3)_2$ 158 | 100 | 17.5 | 35    40 |
| 8 | " | —NH—i-$C_3H_7$ | 100 | piperidine 850 | — | reflux | 2.1 | 52    62 |
| 9 | " | " | 100 | morpholine 2400 | — | reflux | 23 | 43    52 |

*DBN = 1,5-diazabicyclo[3,5,0]-5-nonene
DBU = 1,5-diazabicyclo[4,5,0]-5-undecene

TABLE IV

Physical contants of YCH₂CHOH-CH(OH)-CH₂O-[phenyl with P, Q, H substituents]

| No. | P—Q | Y | IR: $\nu_{max}^{CHCl_3}$ cm$^{-1}$ | NMR: $\delta_{ppm}^{CDCl_3}$ (Hz value shows coupling constant) |
|---|---|---|---|---|
| 1 | [benzo fused ring] | —NHCH(CH₃)₂ | 3300, 1600, 1588, 1404, 1276, 1106, 762. (KBr) | 1.11d(6.5Hz)6H, 2.63-3.13m3H, 3.61brs2H, 3.92-4.39m3H, 6.77 dd(3;8Hz)1H, 7.16-7.57m4H, 7.63-7.88m1H, 8.12-8.37m1H. |
| 2 | [N-SO₂-tosyl indole] | —NHCH(CH₃)₂ (HCl salt) | —3320, 1591, 1370, 1192, 1126.<br>3350, 1592, 1375 1198, 1122(KBr) | 1.28d(6Hz)6H, 2.33s3H, 2.53-3.37m3H, 4.02m3H, 6.95d(0.6Hz) 1H, 7.27-8.0m.(CD₃SOCD₃)<br>0.97d(6.5Hz)6H, 2.29s3H, 2.56-2.90m3H, 3.76-4.20m3H, 6.71-7.92m9H. |
| 3 | [N-SO₂-tosyl indole] | —NHCH(CH₃)₂<br>O—valerate | 3350, 1730, 1372, 1193,1168,1126. | [1.07d(6Hz) + 1.18s]15H, 2.33s 3H, 2.72-3.23m3H, 4.59d(4.5Hz) 2H, 5.03-5.52m1H, 6.57-6.83 m2H, 7.03-7.90m7H. |
| 4 | [N-SO₂-tosyl indole] | COCH₃<br>—N<br>CH(CH₃)₂ | —3400, 1620, 1592, 1371, 1196, 1171, 1129 (KBr) | [1.20d(6.5Hz) + 1.30d(6.5Hz)]6H, 2.20s3H, 2.35s3H, 3.25-4.52m6H, 6.57-7.95m9H. |
| 5 | [N-SO₂-tosyl indole] | CO-[phenyl]<br>—N<br>CH(CH₃)₂ | —3375, 1612, 1600, 1590, 1370, 1192, 1167, 1126 (KBr) | [1.17d(6.5Hz) + 1.21d(6.5Hz)]6H, 2.33s3H, 3.60-4.43m6H, 6.63-6.88m2H, 7.03-7.90m12H. |
| 6 | [N-SO₂-tosyl indole] | COOCH₃<br>—N<br>CH(CH₃)₂ | 3400, 1666, 1592, 1471, 1372, 1190, 1169, 1129 (CHCl₃) | — |
| 7 | [N-SO₂-tosyl indole] | O₂N-[phenyl]<br>S<br>—N<br>CH(CH₃)₂ | 3560, 3450, 1589, 1512, 1364, 1333, 1304, 1190, 1164, 1121. (KBr) | 1.23d(6Hz)6H, 2.33s3H, 3.09-3.35m3H, 3.48-4.41m3H, 6.48-8.36m13H. |
| 8 | [N-SO₂-tosyl indole] | —N[morpholine/piperidine] | 3360, 1591, 1493, 1371, 1188, 1167, 1125. (CHCl₃) | 1.32-1.92m6H, 2.32s3H, 2.22-2.88m6H, 3.80-4.35m5H, 6.63d (8Hz)1H, 6.75d(3.5Hz)1H, 7.05-7.83m7H. |

EXAMPLE IV-1 (AROMATIZATION WITH DBU)

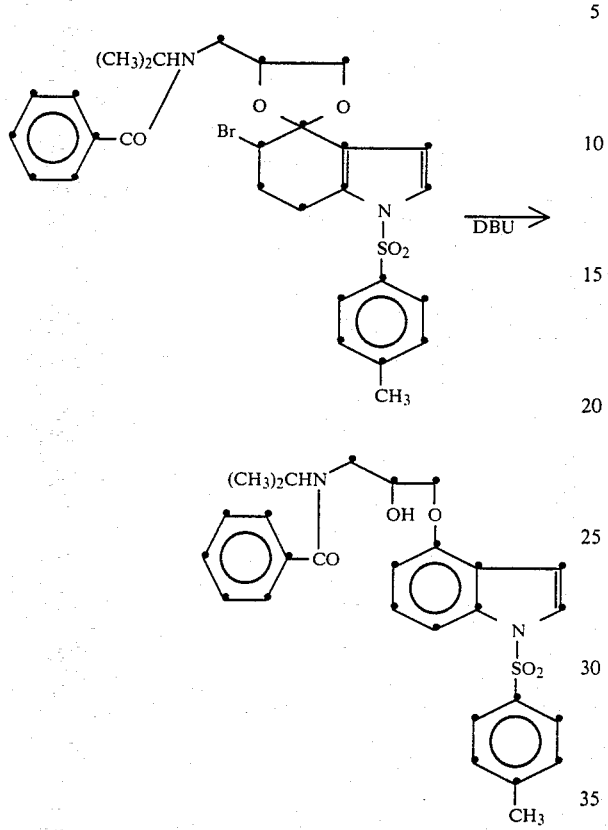

EXAMPLE IV-2 (AROMATIZATION WITH MORPHOLINE)

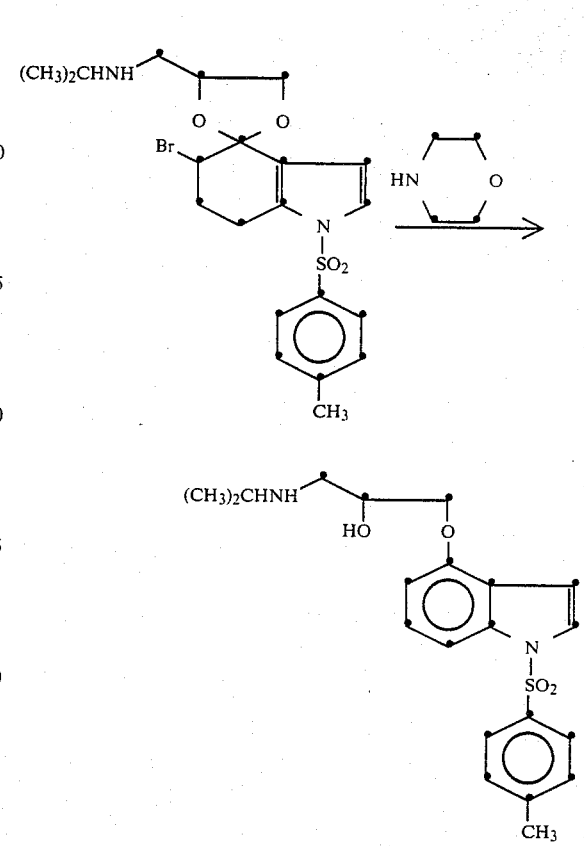

In a three necked flask equipped with a stirrer and a thermometer is added 4'-(N-isopropyl-N-benzoylaminomethyl)-1-p-toluenesulfonyl-5-bromo-4,5,6,7-tetrahydroindole-4-spiro-2'-[1,3]dioxolane (100 parts) and dissolved in a mixture of 1,5-diazabicyclo[5,4,0]-5-undecene (51 parts) and N,N-dimethylformamide (319 parts). After stirring for 24 hours at 85° C., the solution is cooled, diluted with ethyl acetate (300 parts) and washed thrice with water (50 parts). Aqueous washings are combined and washed with ethyl acetate (50 parts). The ethyl acetate solution and ethyl acetate washings are combined, washed with water (30 parts) and dried over anhydrous sodium sulfate (50 parts). After 1 hour, the drying reagent is filtered off and filtrate concentrated to dryness under reduced pressure. Obtained residue (83 parts) is dissolved in ethyl acetate (200 parts), stirred for 30 minutes with active charcoal (10 parts) and filtered through diatomaceous filter-bed. The filtrate concentrated under reduced pressure. The residue is triturated with a small amount of hexane to separate amorphous powder. This is collected by filtration and dried to afford 4-(N-isopropyl-N-benzoyl-3-amino-2-hydroxypropoxy)-1-p-toluenesulfonyl (35 parts) in 41% yield.

In a flask equipped with a reflux condenser is placed 4'-isopropylaminomethyl-5-bromo-1-p-toluenesulfonyl-4,5,6,7-tetrahydroindole-4-spiro-2'-[1,3]dioxolane (100 parts) and morpholine. The solution is refluxed for 20 hours. After cooling, the reaction mixture is concentrated in vacuo to leave resin. Chromatographic purification of the resin affords 4-(3-isopropylamino-2-hydroxypropoxy)-1-p-toluenesulfonylindole (24 parts) in 29% yield. This showed the same physical characteristics with an authentic sample.

EXAMPLE V (AROMATIZATION WITH A LEWIS ACID)

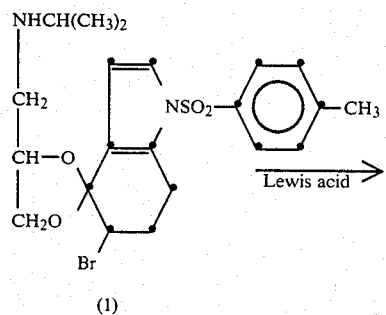

(1)

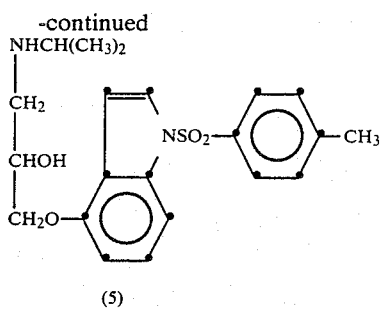

(5)

To a solution of 4'-isopropylaminomethyl-5-bromo-1-p-toluenesulfonyl-4,5,6,7-tetrahydroindole-4-spiro-2'-[1,3]dioxolane (1) (100 parts) and a base as an additional reagent is added a solution of a Lewis acid in a solvent at subzero temperature. The resulting mixture is warmed to room temperature and stirred for the given time. After concentration, the mixture is shaken with aqueous sodium hydroxide and ethyl acetate. The organic layer is taken, washed with water, dried and concentrated. The residue is crystallized from hexane-acetone to give the objective 3-isopropylamino-2-hydroxypropyl 1-p-toluenesulfonyl-4-indolyl ether.

The reaction conditions are illustrated in Table V. Physical constants of the products are given on Table IV.

TABLE V

| No. | Solvent (part by weight) | Lewis acid (molar equivalent) | Additional agent (molar equivalent) | Temperature (°C.) | Time (hour) | Crop (part by weight) | Yield (%) |
|---|---|---|---|---|---|---|---|
| 1 | $CH_2Cl_2$ (25) | $BCl_3$ (1.0) | $N(C_2H_5)_3$ (5.0) | $-60 \to rt$ | 5 | 80 | 83. |
| 2 | $CH_3NO_2$ (71) | $BCl_3$ (1.0) | none | $-15 \to rt$ | 2 | 55 | 65 |
| 3 | $CH_3Ph$ (38) | $BCl_3$ (1.0) | none | " | 13 | / | / |
| 4 | $(CH_2Cl)_2$ (25) | $BCl_3$ (1.0) | $N(C_2H_5)_3$ (1.0) | $-18 \to rt$ | 42 | 27 | 33 |
| 5 | $(CH_2Cl)_2$ (29) | $BBr_3$ (1.0) | $N(C_2H_5)_3$ (1.0) | $-18 \to 0$ | 30 | / | / |
| 6 | $(CH_2Cl)_2$ (29) | $AlCl_3$ (1.0) | none | $0 \to rt$ | 24 | / | / |
| 7 | $(CH_2Cl)_2$ (29) | $AlCl_3$ (1.0) | $N(C_2H_5)_3$ | " | 24 | / | / |
| 8 | $(CH_2Cl)_2$ (8) | $BeCl_2$ (1.0) | $N(C_2H_5)_3$ (2.2) | $-20 \to rt$<br>50 | 31<br>4 | / | / |
| 9 | $(CH_2Cl)_2$ (45) | $SnCl_4$ (3.5) | $N(C_2H_5)_3$ (7.5) | $-78 \to rt$ | 17 | 41 | 48 |
| 10 | $(CH_2Cl)_2$ (25) | $SnCl_4$ (2.5) | $N(C_2H_5)_3$ (10.0) | $-20 \to rt$ | 10 | 39 | 48 |
| 11 | $CH_3Ph$ (25) | $SnCl_4$ (3.5) | $N(C_2H_5)_3$ (10.0) | $-70 \to rt$ | 11 | 21 | 25 |
| 12 | $CH_2Cl_2$ (56) | $SnCl_4$ (3.5) | $N(n-C_8H_{17})_3$ (3.0) | " | 23 | 59 | 70 |
| 13 | $CH_2Cl_2$ (74) | $SnCl_4$ (2.5) | $C_2H_5N(C_6H_{11})_2$ (5.0) | " | 43 | 10 | 12 |
| 14 | $CH_2Cl_2$ (66) | $SnCl_4$ (2.5) | piperidine (4.0) | $-78 \to 5$ | 18 | / | / |
| 15 | $CH_2Cl_2$ (55) | $SnCl_4$ (2.5) | piperazine (4.0) | " | 12 | / | / |
| 16 | $CH_2Cl_2$ (73) | $SnCl_4$ (3.5) | $CH_3N$-morpholine (5.0) | $-70 \to rt$ | 3 | 27 | 33 |
| 17 | $CH_2Cl_2$ (69) | $SnCl_4$ (2.5) | $C_2H_5N$-morpholine (5.0) | $70 \to rt$ | 46 | / | / |
| 18 | $CH_2Cl_2$ (79) | $SnCl_4$ (2.5) | $(CH_3)_2NPh$ (5.0) | " | 43 | / | / |
| 19 | $(CH_2Cl)_2$ (77) | $TiCl_4$ (2.5) | $N(C_2H_5)_3$ (10.0) | $-18 \to rt$ | 15 | 23 | 29 |
| 20 | $(CH_2Cl)_2$ (55) | $TiCl_4$ (3.5) | $N(C_2H_5)_3$ (7.9) | $-70 \to rt$ | 20 | 29 | 35 |
| 21 | $(CH_2Cl)_2$ | $SbCl_5$ (3.5) | $N(C_8H_{17})_3$ (5) | $-18$<br>12 | 1<br>24 | / | / |
| 22 | $(CH_2Cl)_2$ | $SiCl_4$ (3.5) | $N(C_2H_5)_3$ (5) | $-18 \to rt$ | 72 | / | / |

TABLE V-continued

| No. | Solvent (part by weight) | Lewis acid (molar equivalent) | Additional agent (molar equivalent) | Temperature (°C.) | Time (hour) | Crop (part by weight) | Yield (%) |
|---|---|---|---|---|---|---|---|
| 23 | (CH$_2$Cl$_2$) | NbCl$_5$ (3.6) | N(C$_2$H$_5$)$_3$ (5) | −18 → rt | 48 | / | / |
| 24 | (CH$_2$Cl)$_2$ | SbCl$_3$ (3.46) | N(C$_8$H$_{17}$)$_3$ (5) | −18<br>−18 → rt | 3.5<br>17.5 | / | / |
| 25 | (CH$_2$Cl)$_2$ | TeCl$_4$ (3.4) | N(C$_2$H$_5$)$_3$ (5) | −18 → rt | 72 | / | / |
| 26 | CH$_3$NO$_2$ | BeCl$_2$ | none | rt<br>65 | 15<br>7.5 | / | / |
| 27 | CH$_2$Cl$_2$ | ZrCl$_4$ (3.9) | N(C$_2$H$_5$)$_3$ (4) | −17 → rt | 19 | / | 32 |
| 28 | C$_2$H$_5$OC$_2$H$_5$ (3) | SnCl$_4$ (3.5) | N(C$_8$H$_{17}$)$_3$ (5) | −18<br>rt | 1<br>4 | 44.5 | 65.5 |
| 29 | CH$_3$COOC$_2$H$_5$ | SnCl$_4$ (3.5) | N(C$_8$H$_{17}$)$_3$ (5) | −18<br>rt | 1<br>4 | | 42.3 |

(Note)
The blanks space of crop or yield represents that the formation of the product is identified by TLC.
rt = room temperature

EXAMPLE V-1 (AROMATIZATION WITH STANNIC CHLORIDE)

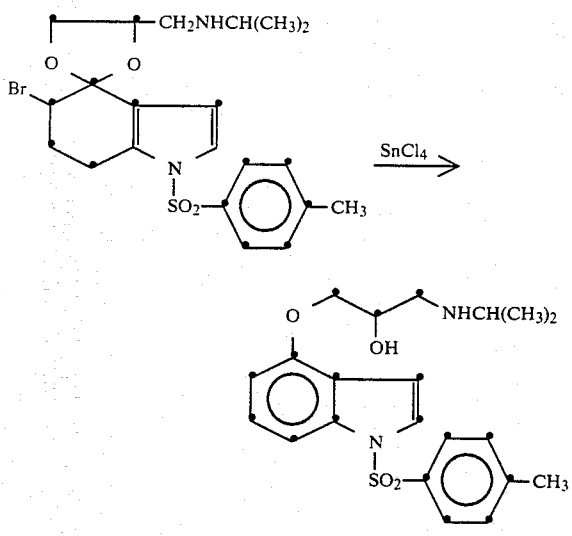

To a solution of 4′-isopropylaminomethyl-5-bromo-1-p-toluenesulfonyl-4,5,6,7-tetrahydroindole-4-spiro-2′-[1,3]dioxolane (100 parts) and triethylamine (143 parts) in dichloromethane (1500 parts) is dropwise added a solution of stannic chloride (80 parts) in dichloromethane (500 parts) at −60° C. with stirring. The mixture is warmed to room temperature, stirred for 5 hours, concentrated and shaken with aqueous 5N-sodium hydroxide and ethyl acetate. The ethyl acetate layer is separated, washed with water, dried over sodium sulfate and concentrated under reduced pressure to give crude product (73 parts) in 87.9% yield. This is triturated in ethyl acetate to give pure 4-(2-hydroxy-3-isopropylaminopropoxy)-1-p-toluenesulfonylindole (56.1 parts) as amorphous solid in 67% yield. NMR: $\delta^{CD_3SOCD_3}$ 0.97d(6.5 Hz)6H, 2.29s3H, 2.56–2.90m3H, 3.76–4.20m3H, 6.71–7.92m9H. (HCl salt of the product) m.p. 225°–226° C. (decomp.). NMR: $\delta^{CD_3SOCD_3}$ 1.28d(6.5 Hz)6H, 2.29s3H, 2.76–3.58m, 3.93–4.53m3H, 5.92brs1H, 6.73–7.00m2H, 7.15–7.96m7H, 9.09brs2H. (HBr salt of the product) m.p. 235°–238° C. (decomp.). (HI salt of the product) m.p. 227.5° C. (decomp.)

EXAMPLE V-2 (AROMATIZATION WITH BORON TRICHLORIDE)

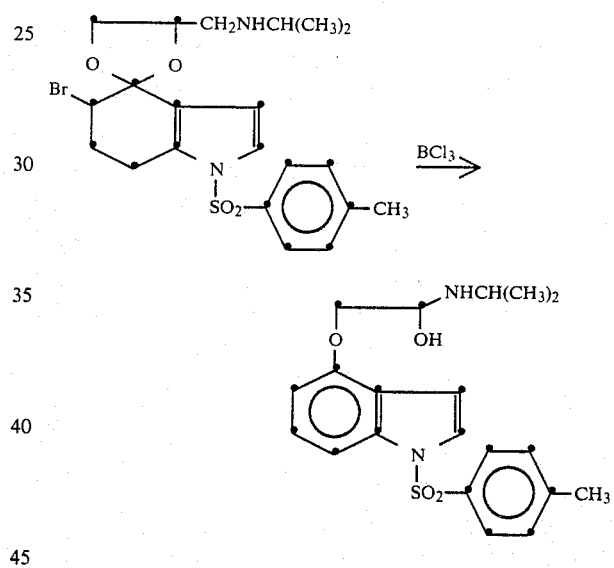

To a solution of 4′-isopropylaminomethyl-5-bromo-1-p-toluenesulfonyl-4,5,6,7-tetrahydroindole-4-spiro-2′-[1,3]-dioxolane (100 parts) in dichloroethane (1000 parts) is added a solution of boron trichloride (2 molar equivalents) in dichloroethane (500 parts) at −19° C. The mixture is allowed to warm to room temperature and to stand for 50 hours. The reaction mixture is washed with aqueous sodium hydroxide at pH 10 and water, dried and concentrated. The residue is crystalized from hexane-benzene to give 4-(2-hydroxy-3-isopropylaminopropoxy)-1-p-toluenesulfonyl indole in 71% yield.

EXAMPLE VI (AROMATIZATION WITH A BASE OR ACID)

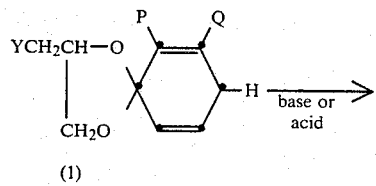

(1)

-continued

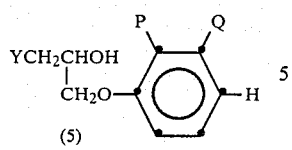

A cyclohexadiene compound (1) is treated with a base under the reaction conditions given in Table VI to afford the corresponding 3-substituted-2-hydroxypropyl aryl ether (5).

-continued

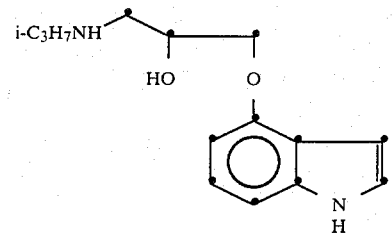

TABLE VI

| | Aromatization | | | | | | |
|---|---|---|---|---|---|---|---|
| | Compound (1) | | | Reagent | Solvent | Temp. | Reaction Time |
| No. | Y | P-Q | Part | (Part) | (Part) | (°C.) | (hr) |
| 1 | —NH—i-$C_3H_7$ | [N-SO₂-C₆H₄-CH₃ vinyl] | 100 | DBU 2 | $CH_2Cl_2$ 266 | 20 | 1 |
| 2 | " | " | 100 | $H_3PO_4$ 1 | [dioxane] 207 | 0 | 1 |
| 3 | " | " | 100 | $SiO_2$ 200 | $CHCl_3$ 300 | 15 | 24 |
| 4 | " | " | 100 | $(C_2H_5)_3N$ 1 | [quinoline] 1000 | 150 | 4 |

EXAMPLE VII (REMOVING A PROTECTING GROUP)

(a) Pindolol

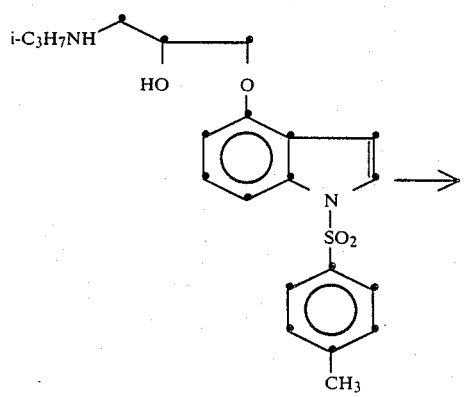

To a solution of 4-(3-isopropylamino-2-hydroxypropoxy)-1-p-toluenesulfonylindole (100 parts) in ethanol (500 parts) placed in a flask equipped with a reflux condenser is added aqueous 1N-sodium hydroxide (36 parts), and the mixture is refluxed for 4 hours. The resulting reaction mixture is acidified with 1N-sulfuric acid (11 parts), concentrated under nitrogen atmosphere until crystallization starts, and kept in a refrigerator overnight. Separated crystals are collected by filtration and washed with diluted ethanol. The crude crystals thus obtained are recrystallized from ethanol to give 4'-(3-isopropylamino-2-hydroxypropoxy)indole as colorless needles (45 parts) in 75.5% yield, m.p. 172°–173° C.

The crystals are identified as pindolol by comparing with a pindolol sample (m.p. 172.5°–173° C.) by mixed melting point determination and comparison of thin-layer chromatograms, IR-spectra and proton-magnetic resonance spectra.

(b) Under conditions similar to (a) above, hydrolysis of Table VII is carried out.

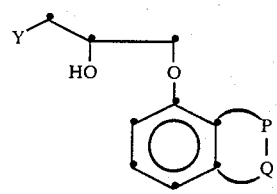
TABLE VII
| | Starting material | | Hydrolysis | | |
|---|---|---|---|---|---|
| Y | | P–Q | Y' | P–Q | mp |
| i-C$_3$H$_7$N—\|CH$_3$CO | | [N-SO$_2$-tolyl vinyl] | i-C$_3$H$_7$NH— | [NH vinyl] | 173° |
| i-C$_3$H$_7$N—\|t-C$_4$H$_9$CO | | " | " | " | " |
| [Ph-CO-N(i-C$_3$H$_7$)—] | | " | " | " | " |
| [CH$_3$-C$_6$H$_4$-SO$_2$-N(i-C$_3$H$_7$)—] | | " | " | " | " |
| [o-NO$_2$-C$_6$H$_4$-S-N(i-C$_3$H$_7$)—] | | " | " | " | " |
| i-C$_3$H$_7$N—\|t-C$_4$H$_9$OCO | | [N-CHO vinyl] | " | " | " |
| i-C$_4$H$_9$N—\|CH$_3$CO | | [N-COCH$_3$ vinyl] | i-C$_4$H$_9$NH— | " | 154–156° |
| i-C$_3$H$_7$NH— | | [N-SO$_2$-tolyl C(CH$_3$)=] | i-C$_3$H$_7$NH— | [NH C(CH$_3$)=] | 95–97° |

TABLE VII-continued

| Starting material | | Hydrolysis | | |
|---|---|---|---|---|
| Y | P-Q | Y' | P-Q | mp |
| t-C$_4$H$_9$NH— | ![structure with N-COCH3 and CH3] | t-C$_4$H$_9$NH— | " | 131–133° |

EXAMPLE VII (CONTINUOUS REACTIONS)

(a) 6-(3-Isopropylamino-2-hydroxypropoxy)benzothiazole

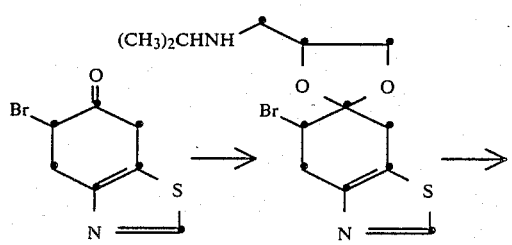

A mixture of 6-oxo-5-bromo-4,5,6,7-tetrahydrobenzothiazole (100 parts), 3-isopropylamino-1,2-propanediol (67 parts), p-toluenesulfonic acid monohydrate (99 parts) and toluene (1550 parts) is heated under reflux for 21 hours while drying the refluxing azeotropic mixture according to the method described in Example I. After cooling, the reaction mixture is adjusted to pH 9 by adding aqueous 2.5N-sodium hydroxide and formed organic layer is separated. The organic layer is washed with water, dried over anhydrous sodium sulfate, and concentrated under reduced pressure. The remaining 4'-isopropylaminomethyl-5-bromo-4,5,6,7-tetrahydrobenzothiazole-6-spiro-2'-[1,3]-dioxolane (156 parts) is dissolved in piperidine (1560 parts), and stirred for 49 hours on an oil bath heated at 95° to 100° C. The reaction mixture is concentrated under reduced pressure to leave residue which is mixed with ethyl acetate and water, shaken and fractionated to separate formed organic layer. The organic layer is washed with water, dried over anhydrous sodium sulfate, and concentrated under reduced pressure. Residue (172 parts) is recrystallized from ethanol-hydrochloric acid giving 6-(3-isopropylamino-2-hydroxypropoxy)-benzothiazole (65 parts) in 57% yield. mp. 132°–134° C. (hydrochloride trihydrate).

(b) According to Examples I to V combined, a series of reactions is carried out in a manner similar to above (a) to give the compounds listed in Table VIII.

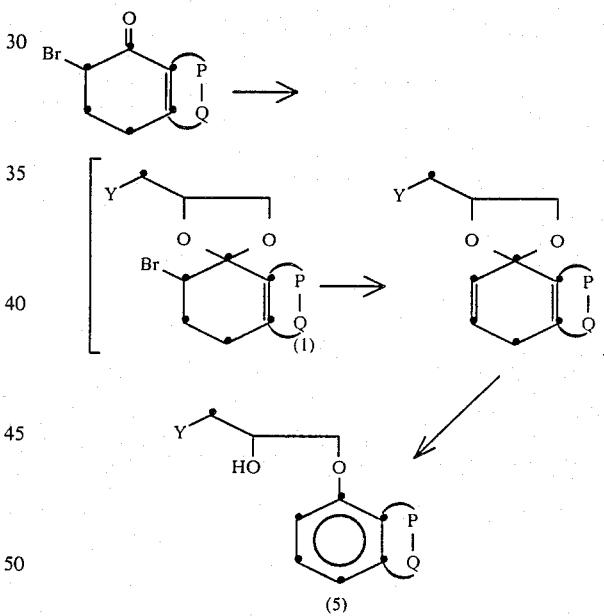

TABLE VIII

| No. | P—Q | Y | mp | Elemental Analysis | | |
|---|---|---|---|---|---|---|
| | | | | C | H | N |
| 1 | ![structure with N-H] | —NH—i-C$_3$H$_7$ | mp 172~173° | Calcd. 66.71<br>Found 66.67 | 8.12<br>8.02 | 11.28<br>11.41 |
| 2 | " | —NHCH$_2$CH(CH$_3$)$_2$ | mp 154~156° | Calcd. 68.67<br>Found 68.85 | 8.45<br>8.35 | 10.68<br>10.68 |

TABLE VIII-continued

| No. | P—Q | Y | mp | Elemental Analysis | C | H | N |
|---|---|---|---|---|---|---|---|
| 3 | 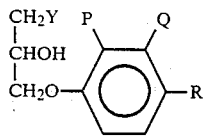 | —NH—i-C$_3$H$_7$ | mp 95~97° | Calcd. | 68.67 | 8.45 | 10.68 |
|   |     |                 |           | Found  | 68.65 | 8.65 | 10.77 |
| 4 | "   | —NH—t-C$_4$H$_9$ | mp 131~133° | Calcd. | 69.53 | 8.75 | 10.14 |
|   |     |                 |             | Found  | 69.54 | 8.59 | 10.20 |
| 5 | 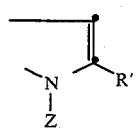 | —NH—i-C$_3$H$_7$ .HCl | mp 89° / mp 147~148° (HCl) | Calcd. / Found | 63.48 / 63.59 | 7.81 / 7.90 | 4.94 / 4.83 |
| 6 | 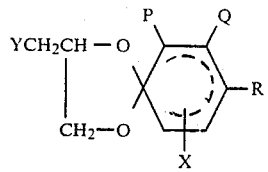 | —NH—t-C$_4$H$_9$ .HCl | mp 277~278° (HCl) | Calcd. | 58.44 | 7.66 | 8.52 |
|   |     |                 |             | Found  | 58.54 | 7.53 | 8.50 |
| 7 | "   | —Cl             | mp 157~158° | Calcd. | 56.35 | 5.52 | 5.48 |
|   |     |                 |             | Found  | 56.33 | 5.51 | 5.64 |
| 8 | "   | —Br             | mp 133~135° | Calcd. | 48.02 | 4.70 | 4.67 |
|   |     |                 |             | Found  | 48.09 | 4.59 | 4.64 |

What I claim is:

1. A process for preparing a compound of the formula

[formula: CH$_2$Y—CHOH—CH$_2$O— attached to a benzene ring bearing P, Q, R]

wherein
one of P and R combined with Q represents

[formula showing N(Z)—C(R')=]

in which R' is hydrogen or lower alkyl, and
Z is hydrogen, lower alkanoyl, lower alkyl sulfonyl, C$_6$–C$_{10}$ aroyl or C$_6$–C$_{10}$ arylsulfonyl, and
the remaining P or R is hydrogen or halogen, and Y is halogen, hydroxy, C$_6$–C$_{10}$ arylsulfonyloxy, amino, lower alkylamino, C$_6$–C$_{10}$ aryl lower alkylamino, lower acyl amino wherein the acyl group is from a carboxylic, sulfonic, sulfenic, phosphoric or carbonic acid, di-lower alkylamino, lower alkyleneamino, N-lower alkyl-N-C$_6$–C$_{10}$ aryl lower alkylamino, di-lower acylamino wherein the acyl group is from a carboxylic, sulfonic, sulfenic, phosphoric or carbonic acid, N-lower alkyl-N-lower acylamino wherein the acyl group is from a carboxylic, sulfonic, sulfenic, phosphoric or carbonic acid, or N-tri-lower alkylsilylamino,
which comprises subjecting a compound of the formula

[formula: YCH$_2$CH—O and CH$_2$—O attached to ring bearing P, Q, R, X]

wherein Y, P, Q and R are as defined above and X is hydrogen or halogen, and the dotted line represents the presence of one or two double bonds to aromatization.

2. A process according to claim 1 for the preparation of a compound of the formula

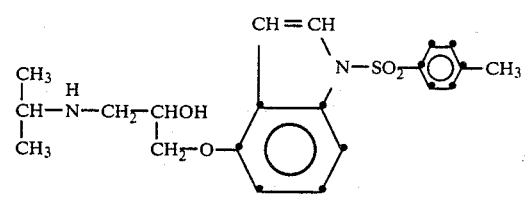

which comprises subjecting a compound of the formula

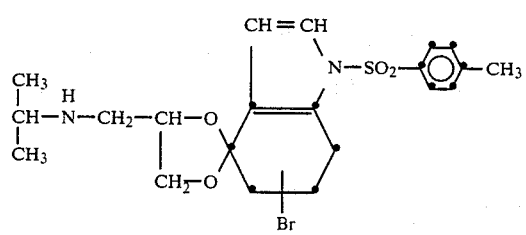

to aromatization.

3. A process claimed in claim 1 wherein the aromatization is carried out by the action of a secondary amine.

4. A process claimed in claim 1 wherein the secondary amine is morpholine or piperidine and the reaction is carried out at 80° C. to 150° C.

5. A process claimed in claim 1 wherein the aromatization is carried out by the action of a Lewis acid.

6. A process claimed in claim 5 wherein the Lewis acid is one selected from stannic chloride, boron trichloride and titanium chloride.

7. A process claimed in claim 5 wherein the aromatization is carried out in the presence of a tertiary amine.

8. A process claimed in claim 7 wherein the tertiary amine is triethylamine, tributylamine, trioctylamine, quinuclidine or 1,4-diazabicyclo[2,2,2]octane.

9. A process claimed in claim 5 wherein Y is lower alkylamino or lower alkyleneamino.

10. A process claimed in claim 1 wherein the aromatization is carried out by the action of a mineral acid or adsorbent.

* * * * *